United States Patent [19]

Wikel, II

[11] 4,434,288

[45] Feb. 28, 1984

[54] PREPARATION OF SUBSTITUTED 1-THIAZINYL OR 1-THIAZOLYL-2-AMINOBENZIMIDAZOLES

[75] Inventor: James H. Wikel, II, Greenwood, Ind.

[73] Assignee: Eli Lilly and Company, Indianapolis, Ind.

[21] Appl. No.: 366,883

[22] Filed: Apr. 8, 1982

[51] Int. Cl.$^3$ ............................................. C07D 235/30
[52] U.S. Cl. ........................................ 544/54; 544/55; 548/181; 542/454
[58] Field of Search ............................. 544/54, 55, 53; 548/181; 542/454

[56] References Cited

U.S. PATENT DOCUMENTS

| | | | |
|---|---|---|---|
| 3,825,537 | 7/1974 | Haugwitz et al. | 260/243 R |
| 4,008,243 | 2/1977 | Wikel et al. | 260/306.7 T |
| 4,018,790 | 4/1977 | Paget et al. | 260/309.2 |
| 4,118,573 | 10/1978 | Paget et al. | 548/306 |
| 4,118,742 | 10/1978 | Paget et al. | 548/306 |
| 4,150,028 | 4/1979 | Paget et al. | 260/306.7 T |
| 4,174,454 | 11/1979 | Paget et al. | 548/306 |
| 4,196,125 | 4/1980 | Paget et al. | 548/141 |
| 4,216,313 | 8/1980 | Paget et al. | 544/55 |
| 4,230,868 | 10/1980 | Paget et al. | 548/306 |

OTHER PUBLICATIONS

Wright, Chem. Reviews, 48, 486–487 (1951).
Price, et al., "Some Sulfondamide Derivatives of 2-Aminobenzimidazole," J. Org. Chem. 12, 269–274 (1947).

Primary Examiner—Robert W. Ramsuer
Attorney, Agent, or Firm—Karen B. Dow; Arthur R. Whale

[57] ABSTRACT

This invention concerns a process for preparing 2-amino-1,5(6)-substituted-benzimidazole compounds by reacting a 1-unsubstituted-2-amino-5(6)-substituted-benzimidazole compound with a sulfonyl chloride or a haloalkyl isothiocyanate in the presence of an alkali metal hydroxide or carbonate, water, and a water-miscible nonhydroxylic solvent.

8 Claims, No Drawings

PREPARATION OF SUBSTITUTED 1-THIAZINYL OR 1-THIAZOLYL-2-AMINOBENZIMIDAZOLES

This invention describes a process for preparing 2-amino-1,5(6)-substituted-benzimidazole compounds by reacting a 1-unsubstituted-2-aminobenzimidazole with a sulfonyl chloride or a haloalkyl isothiocyanate in the presence of an alkali metal hydroxide or carbonate, water, and a water-miscible nonhydroxylic solvent.

BACKGROUND OF THE INVENTION

1-Substituted-2-aminobenzimidazole compounds inhibit the growth of certain viruses, such as rhinoviruses, polio (types I, II, III), Coxsackie (A9, A21, B5), echo virus (strains 1, 2, 3, 4), and Mengo virus. Certain sulfonylbenzimidazole antiviral compounds are disclosed in U.S. Pat. Nos. 4,118,742 and 4,174,454.

The preparation of these compounds in the above references follows the methods disclosed in U.S. Pat. Nos. 4,018,790 and 4,118,573. Both of these patents reveal the reaction of a benzimidazole compound and a sulfonyl chloride compound in an organic solvent, preferably using a hazardous base such as sodium hydride. The patents do not divulge the use of an aqueous solution as in the presently claimed process.

Certain thiazolinyl or thiazinyl benzimidazole compounds are disclosed in U.S. Pat. Nos. 4,008,243 and 4,150,028 as antiviral agents. However, the process disclosed for their preparation is different from the novel claimed process of this application.

In Chemical Reviews, 48, 397–541 (1951), John B. Wright reports that the imidazole ring of benzimidazole compounds is cleaved by an acid halide and water to form the diamine compound.

Charles Price and Robert Reitsema in "Some Sulfonamide Derivatives of 2-Aminobenzimidazole", *Journal of Organic Chemistry*, 12, 269–274 (1947) describe the formation of 2-aminobenzimidazole-3-nitrobenzesulfonate by treating 1-(3-nitrophenylsulfonyl)-2-aminobenzimidazole with sodium hydroxide and acetic acid.

Copending application, Ser. No. 366,759, filed of even date herewith, claims a process for removing a sulfonyl substituent from the 1-position of 2-amino-5-substituted-benzimidazole to form the corresponding tautomeric benzimidazole. Another copending application, Ser. No. 366,760, also filed of even date herewith, describes a series of 5- and 6-substituted-ethylenicbenzimidazole compounds.

SUMMARY OF THE INVENTION

This invention concerns a process for preparing 2-amino-1,5(6)-substituted-benzimidazole compounds by reacting a 1-unsubstituted-2-aminobenzimidazole compound with a sulfonyl chloride or a haloalkyl isothiocyanate in the presence of an alkali metal hydroxide or carbonate, water, and a water-miscible nonhydroxylic solvent at a temperature from about 0° C. to about 75° C. The prepared benzimidazoles are useful as antivirals.

DETAILED DESCRIPTION AND PREFERRED EMBODIMENTS

The present invention relates to a new process for the preparation of 1-substituted-2-amino-5(6)-substituted-benzimidazole compounds of the formula I.

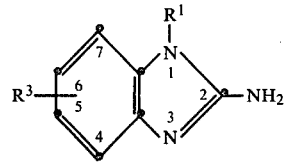

A tautomeric benzimidazole compound of the formula II

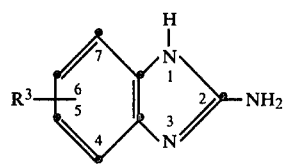

is reacted with a second reactant, either a sulfonyl halide of the formula $R^2SO_2X$; or a haloalkyl isothiocyanate of the formula $X(CH_2)_nNCS$, optionally substituted on the carbon chain; in the presence of an alkali metal hydroxide or carbonate, water, and a water-miscible nonhydroxylic solvent at a temperature from about 0° C. to about 75° C. to form the compound of formula I.

$R^1$ in the above formula is

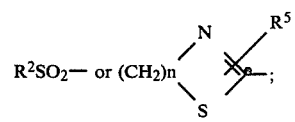

$R^2$ is $C_1$–$C_5$ alkyl, $C_3$–$C_7$ cycloalkyl, phenyl, furyl, or thienyl;

$R^3$ is at the 5- or 6-position and is hydrazinocarbonyl, carboxy, carboxamido, N-($C_1$–$C_4$ alkyl)carboxamido, hydroxymethyl, cyano, nitro, $C_1$–$C_4$ alkyl, $C_1$–$C_4$ alkoxy, $C_1$–$C_4$ alkylthio, methylsulfonyl, phenylthio, phenylsulfinyl, phenoxy, trifluoromethyl, $C_1$–$C_8$ alkoxycarbonyl, allyloxycarbonyl, propargyloxycarbonyl, ($C_3$–$C_7$ cycloalkyl)oxycarbonyl, ($C_3$–$C_7$ cycloalkyl)methoxycarbonyl, 1-($C_3$–$C_7$ cycloalkyl)ethoxycarbonyl, benzyloxycarbonyl, α-methylbenzyloxycarbonyl, phenoxycarbonyl, $C_1$–$C_8$ alkoxycarbonylmethyl, 1-($C_1$–$C_8$ alkoxycarbonyl)ethyl,

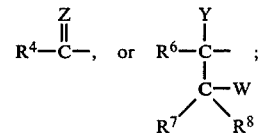

$R^4$ is hydrogen, $C_1$–$C_7$ alkyl, $C_3$–$C_7$ cycloalkyl, ($C_3$–$C_7$ cycloalkyl)methyl, 1-($C_3$–$C_7$ cycloalkyl)ethyl, thienyl, benzyl, phenyl, or mono-substituted phenyl wherein said substituent is selected from the group consisting of $C_1$–$C_4$ alkyl, $C_1$–$C_4$ alkoxy, chloro, bromo, iodo, nitro, and trifluoromethyl;

$R^5$ is hydrogen, $C_1$–$C_3$ alkyl, benzyl, or phenyl;

$R^6$ is hydrogen, $C_1$–$C_7$ alkyl, $C_3$–$C_7$ cycloalkyl, ($C_3$–$C_7$ cycloalkyl)methyl, 1-($C_3$–$C_7$ cycloalkyl)ethyl, phenyl, or mono-substituted phenyl, wherein said phenyl substituent is selected from the group consisting of $C_1$–$C_4$ alkyl, $C_1$–$C_4$ alkoxy, chloro, bromo, iodo, nitro, and trifluoromethyl;

$R^7$ and $R^8$ independently are hydrogen, halo, cyano, hydroxymethyl, nitro,

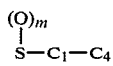

alkyl, $CH_2R^9$, $COR^9$, phenyl or mono-substituted phenyl, wherein said phenyl substituent is selected from the group consisting of $C_1$–$C_4$ alkyl, $C_1$–$C_4$ alkoxy, chloro, bromo, iodo, nitro, and trifluoromethyl;

$R^9$ is hydroxy, $C_1$–$C_4$ alkoxy, $C_3$–$C_6$ cycloalkyl-$C_1$–$C_4$ alkoxy, or (O—$C_1$–$C_4$ alkyl)$_p$$NR^{10}R^{11}$;

$R^{10}$ and $R^{11}$ independently are hydrogen or $C_1$–$C_4$ alkyl;

Z is oxygen, $C_1$–$C_4$ alkoxyimino, or $C_1$–$C_7$ alkylidene;

X is chloro or bromo;

Y is hydrogen and W is hydroxy, or together Y and W form a bond;

m is 0, 1, or 2;

n is 2 or 3; and p is 0 or 1.

The following definitions refer to the various terms used throughout this disclosure. The term "thienyl" refers to the thiophene radical attached at the 2- or 3-position. The term "furyl" refers to the furan radical attached at the alpha or beta position.

The term "$C_1$–$C_7$ alkyl" refers to the straight and branched aliphatic radicals of one to seven carbon atoms including methyl, ethyl, propyl, isopropyl, butyl, isobutyl, sec-butyl, tert-butyl, amyl, isoamyl, sec-amyl, sec-isoamyl (1,2-dimethylpropyl), tert-amyl (1,1-dimethylpropyl), neopentyl, hexyl, isohexyl (4-methylpentyl), sec-hexyl (1-methylpentyl), 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, heptyl, isoheptyl (5-methylhexyl), sec-heptyl (1-methylhexyl), 1-ethylpentyl, 2,2-dimethylpentyl, 3,3-dimethylpentyl, 4,4-dimethylpentyl, 1,2-dimethylpentyl, 1,4-dimethylpentyl, 1,2,3-trimethylbutyl, 1,1,2-trimethylbutyl, 1,1,3-trimethylbutyl, and the like. The term $C_1$–$C_7$ alkyl includes within its definition the terms $C_1$–$C_3$ alkyl, $C_1$–$C_4$ alkyl, and $C_1$–$C_5$ alkyl.

The term "$C_3$–$C_7$ cycloalkyl" refers to the saturated alicyclic rings of three to seven carbon atoms such as cyclopropyl, methylcyclopropyl, cyclobutyl, cyclopentyl, cyclohexyl, 1-, 2-, 3- or 4-methylcyclohexyl, cycloheptyl, and the like.

The term "$C_1$–$C_4$ alkoxy" refers to the alkyl radicals of one to four carbon atoms attached to the remainder of the molecule by oxygen such as methoxy, ethoxy, propoxy, and the like. The term "$C_1$–$C_4$ alkoxyimino" refers to a bivalent =N-O($C_1$–$C_4$ alkyl) group such as methoxyimino, ethoxyimino, propoxyimino, and the like. The term "$C_1$–$C_8$ alkoxycarbonyl" refers to a

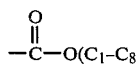

alkyl) group, where an alkoxy group of one to eight carbon atoms is attached to the remainder of the molecule by a carbonyl group such as methoxycarbonyl, ethoxycarbonyl, propoxycarbonyl, and the like.

The term "$C_1$–$C_4$ alkylthio" refers to the alkyl radicals of one to four carbon atoms attached to the remainder of the molecule by sulfur such as methylthio, ethylthio, propylthio, and the like.

The term "$C_1$–$C_7$ alkylidene" refers to divalent organic radicals of one to seven carbon atoms derived from the corresponding aliphatic hydrocarbons in which two hydrogen atoms are taken from the same carbon atom, such as ethylidene, propylidene, butylidene, pentylidene, and the like.

The terms "halo" and "halide" refer to chloro, bromo, iodo, chloride, bromide, and iodide.

The term "tautomeric benzimidazole" refers to a benzimidazole reagent which can be substituted at either nitrogen atom with a hydrogen atom. The benzimidazole reactant, unsubstituted on nitrogen and bearing an $R^3$ substituent group at the 5-position of the benzene moiety, has a corresponding tautomeric form with which it is in equilibrium wherein the substituent resides alternatively at the 6-position. The isomer mixture can be indicated by numbering the alternate positions as 5(6). As a consequence of such tautomerism, the reaction of a 5(6)-substituted benzimidazole with a sulfonyl halide or haloalkyl isothiocyanate produces isomeric mixtures of 1,5(6)-substituted benzimidazoles.

In the above reaction the benzimidazole reactants are compounds (II) bearing $R^3$ substituents which are chemically inert to the second reactant. The benzimidazole compound and the second reactant can be employed in approximately equimolar quantities. However, a slight excess of the second reactant is preferred. An excess of either reactant can be used if desired without adverse effects on the yield of product.

Preferred second reactants are sulfonyl halides, with the most preferred being isopropylsulfonyl chloride. Preferred benzimidazole reactants are those in which $R^3$ is

and $R^4$ is phenyl and Z is oxygen.

The 1-unsubstituted benzimidazole, is dissolved in the solvent, water, and base. Then the sulfonyl halide or haloalkyl isothiocyanate is added slowly to minimize fuming and to avoid a large exotherm. The mixture is stirred and then allowed to stand before the product is collected.

The reaction can be carried out in any water-miscible nonhydroxylic solvent (one that does not contain hydroxyl groups), including acetone, dimethoxyethane (glyme, DME), tetrahydrofuran (THF), tertiary amides such as N,N-dimethylformamide (DMF), and the like. The preferred solvent is acetone. Any mixture of the above solvents may also be used. The addition of the immiscible solvent is permitted as long as the entire solvent system is water miscible.

The reaction medium also contains base to serve as an acid-binding agent; enough base must be added to completely neutralize the hydrogen halide formed as a by-product. The base used is an alkali metal hydroxide or carbonate, such as sodium hydroxide, potassium hydroxide, sodium carbonate, potassium carbonate, and the like. The preferred base is sodium hydroxide.

Water is also in the reaction mixture. The ratio of solvent to water must be sufficient to allow all the reactants to go into solution. This ratio of solvent to water is from about 1:1 to about 6:1 and preferably 1:1.

The reaction is best carried out at a temperature from about 0° C. to about 75° C. Preferably, the reaction is carried out at ambient temperature or from about 20° C. to about 30° C.

The product of the reaction is a 1,5(6)-substituted-2-aminobenzimidazole compound, hereinafter called the substituted benzimidazole compound. In those instances where the product precipitates, it may be isolated by filtering the reaction mixture. Alternatively, the reaction mixture may be concentrated to induce crystallization. Or the reaction mixture can be evaporated to dryness and the residue dissolved in a suitable solvent such as acetone or methanol to separate and remove any insoluble material. The acetone or methanol solution containing the substituted benzimidazole compound is concentrated to crystallize the product or it is evaporated to give a second residue, which is then dissolved in methanol for example. The substituted benzimidazole compound is recovered from the methanol by crystallization.

The reaction of the tautomeric benzimidazole compound and the second reactant in this process usually provides about a 1:1 mixture of 1,5- and 1,6-substituted-benzimidazole isomers. The isomers are separable by fractional crystallization or by column chromatography. Usually the 6-isomer crystallizes first from a solution of the mixture. The isomers can be identified by their nuclear magnetic resonance spectra in the phenyl proton region (7.0 to 8.3 ppm).

The preparation of the benzimidazole and sulfonyl halide starting materials for use in the claimed process is taught in U.S. Pat. Nos. 4,018,790 and 4,118,573. The preparation of haloalkyl isothiocyanates is taught in U.S. Pat. No. 4,008,243. Such teachings are incorporated herein by reference.

The following examples are illustrative of this invention and are not to be considered as limitations on it.

EXAMPLE 1

2-amino-5(6)-benzoyl-1-(thiazin-2-yl)benzimidazole

Three grams (0.0127 moles) of 2-amino-5(6)-benzoylbenzimidazole was dissolved in 30 ml. of acetone with 30 ml. of water and 13 ml. of 1 N sodium hydroxide. Added to the above solution was 2.5 g. (0.0139 moles) of 3-bromopropylisothiocyanate. The solution was stirred at room temperature for 2 hours and allowed to stand over the weekend at room temperature.

The precipitate which had formed was collected. Thin layer chromatography (TLC) (25:6:1 or 15:4:1 methylene dichloride:ethyl acetate:acetic acid) indicated that the precipitate was a mixture of 5- and 6-isomers. Proton NMR also indicated the two isomers as products. The yield was 2.68 g. or 63%. The $R_f$ (retention factor) ratio was less than 0.3.

EXAMPLE 2

2-amino-5(6)-benzoyl-1-isopropylsulfonylbenzimidazole

Slurried in 15 ml. of water was 3.6 g. (0.015 moles) of 2-amino-5(6)-benzoylbenzimidazole. Added to the benzimidazole-water mixture were 17 ml. of 1 N sodium hydroxide and 15 ml. of acetone with stirring. After the above ingredients were completely in solution, 1.8 ml. (2.3 g; 0.016 moles) of isopropylsulfonyl chloride was added portionwise with vigorous stirring. The entire solution was stirred at room temperature for 2 hours. The tan solid which precipitated was filtered and washed with water and then ether. The yield was 3.7 g. or 72%.

Thin layer chromatography (ethyl acetate/silica gel) indicated a mixture of the 5- and 6-isomers in the solid. Proton NMR also indicated a mixture of isomers. The following elemental analysis was obtained:

Calculated for $C_{17}H_{17}N_3O_3S$:

Theory: C, 59.46; H, 4.99; N, 12.24. Found: C, 59.40; H, 5.15; N, 12.44.

EXAMPLE 3

2-amino-5(6)-cyclopropylcarbonyl-1-isopropylsulfonyl benzimidazole

Two grams (0.01 moles) of 2-amino-5(6)-cyclopropylcarbonylbenzimidazole was dissolved in 10 ml. of water with 10 ml. of 1 N sodium hydroxide and sufficient acetone to obtain a complete solution. Added to the solution, with stirring, was 1.2 ml. of isopropylsulfonyl chloride. The entire solution was stirred for 1 hour and then allowed to stand overnight. The precipitate which formed was filtered, washed with water, and crystallized from methanol. The yield was 0.96 g. or 31%. Proton NMR and IR indicated a mixture of 5- and 6-isomers. The melting point was 162°-165° C. with decomposition. The following elemental analysis was obtained:

Calculated for $C_{14}H_{17}N_3O_3S$:

Theory: C, 54.71; H, 5.58; N, 13.67. Found: C, 54.76; H, 5.48; N, 13.47.

EXAMPLE 4

2-amino-5(6)-cyclohexylcarbonyl-1-isopropylsulfonyl-benzimidazole

Six grams (0.0185 moles) of 2-amino-5(6)-cyclohexylcarbonylbenzimidazole hydrobromide was stirred in 50 ml. of water with 38 ml. of 1 N sodium hydroxide. After 15 minutes, 50 ml. of acetone was added. Then 2.3 ml. (0.020 moles) of isopropylsulfonyl chloride was added dropwise with stirring to the mixture. The entire solution was left at room temperature for 2 hours. A dark oil was recovered from the mixture by decanting the aqueous phase. Thin layer chromatography (ethyl acetate) indicated that the dark oil was the desired product. The oil was dissolved in methanol and treated with carbon. The oil mixture was then absorbed on a dry column of silica gel. The dry column was eluted with a 75:25 mixture of chloroform and ethyl acetate. A brown solid foam was obtained in a yield of 2.65 grams or 41%. Proton NMR and IR indicated a mixture of 5- and 6-isomers. The melting point was 65°-80° C. with decomposition. The following elemental analysis was obtained:

Calculated for $C_{17}H_{23}N_3O_3S$:

Theory: C, 58.43; H, 6.63; N, 12.02. Found: C, 58.41; H, 6.42; N, 11.81.

EXAMPLE 5

2-amino-5(6)-cyano-1-(2-thienylsulfonyl)benzimidazole

Dissolved 4.1 g. (0.026 moles) of 2-amino-5(6)-cyanobenzimidazole in 100 ml. of acetone. The mixture was diluted with 150 ml. of water. Added to the mixture, with stirring, was 15 ml. of 2 N sodium hydroxide and 5 g. (0.027 moles) of 2-thiophene sulfonyl chloride in 10 ml. of acetone. The precipitate was collected after two hours.

The yield was 5.6 g. or 71%. Proton NMR and UV indicated a mixture of 5- and 6-isomers. The following elemental analysis was obtained:

Calculated for $C_{12}H_8N_4S_2O_2$:

Theory: C, 47.36; H, 2.65; N, 18.41. Found: C, 47.32; H, 2.93; N, 18.72.

EXAMPLE 6
2-amino-5(6)-benzoyl-1-isopropylsulfonylbenzimidazole

Three grams (0.013 moles) of 2-amino-5(6)-benzoylbenzimidazole was dissolved in 50 ml. of tetrahydrofuran with 50 ml. of water and 7 ml. of 2 N sodium hydroxide. Then 1.7 ml. of isopropylsulfonyl chloride was added dropwise. After two hours at room temperature, the tetrahydrofuran was removed under vacuum. The residual oil, which was formed, was triturated with acetone and water.

The yield was 2.14 g. or 48%. Proton NMR indicated a mixture of 5- and 6-isomers. The following elemental analysis was obtained:

Calculated for $C_{17}H_{17}N_3SO_3$:

Theory: C, 59.46; H, 4.99; N, 12.24. Found: C, 59.70; H, 4.86; N, 12.41.

EXAMPLE 7
2-amino-5(6)-methyl-1-isopropylsulfonylbenzimidazole

An amount of 14.7 g. (0.1 moles) of 2-amino-5(6)-methylbenzimidazole was dissolved in a mixture of 200 ml. of acetone and 250 ml. of water. Then 100 ml. of 1 N sodium hydroxide was added, followed by 12.5 ml. (15.6 g.; 0.11 moles) of isopropylsulfonyl chloride with stirring. After about two hours at room temperature, 1 l. of water was added, with stirring, until the solution was cloudy is order to induce crystallization. The product was then collected by filtration and the yield was 6.2 g. (24%) of the isomer mixture.

The NMR spectra was consistent with the expected structure.

The following elemental analysis was obtained:

Calculated for $C_{11}H_{15}N_3SO_2$:

Theory: C, 52.15; H, 5.97; N, 16.59. Found: C, 52.10; H, 5.97; N, 16.35.

EXAMPLE 8
2-amino-5(6)-propanoyl-1-isopropylsulfonylbenzimidazole

A slurry of 45.6 g. (0.24 mole) of 2-amino-5(6)-propanoylbenzimidazole was made in 400 ml. of acetone and 400 ml. of water. Then 260 ml. of 1 N sodium hydroxide was added, followed by the dropwise addition of 30 ml. of isopropylsulfonyl chloride with vigorous stirring. After about 4 hours of stirring at room temperature, the precipitate formed was filtered, and then washed with water.

The yield was 46 g. or 65% of the 5(6)-isomer mixture. The 6-isomer was recrystallized from 1800 ml. of methyl isobutyl ketone, giving a yield of 24.5 g. (35%). The mass spectrum indicated the expected molecular ion at m/e=295. In addition, the following elemental analysis was obtained:

Calculated for $C_{13}H_{17}N_3O_3S$:

Theory: C, 52.87; H, 5.80; N, 14.23. Found: C, 52.78; H, 5.54; N, 14.41.

EXAMPLE 9
2-amino-5(6)-propanoyl-1-isopropylsulfonylbenzimidazole

To a solution of 840 ml. of acetone and 408 ml. of water was added 45.6 g. (0.24 moles) of 2-amino-5(6)-propanoylbenzimidazole. The resulting mixture was a slurry, to which was added dropwise 120 ml. (0.24 moles) of 2 N sodium hydroxide. Upon addition of the base, the solid went into solution. A solution of 35 ml. of acetone and 30 ml. of isopropylsulfonyl chloride was added dropwise. Upon stirring a solid (A) was formed, filtered off, and set aside to dry. The yield of A was 17.6 g., and NMR indicated that A was pure 6-isomer. The mass spectrum indicated the expected molecular ion at m/e=295. The following elemental analysis was obtained:

Calculated for $C_{13}H_{17}N_3O_3S$:

Theory: C, 52.87; H, 5.80; N, 14.23. Found: C, 53.06; H, 5.77; N, 14.43.

The remaining solution was stirred overnight and another solid (B) was obtained, and set aside to dry. The yield of B was 15.37 g. NMR indicated that B was a mixture of 5- and 6-isomers.

The solution was again stirred, resulting in another solid (C) of yield 11.47 g. NMR indicated that C was mainly the 5-isomer, and the mass spectrum showed the expected ion at m/e=295. The following elemental analysis was obtained:

Calculated for $C_{13}H_{17}N_3O_3S$:

Theory: C, 52.87; H, 5.80; N, 14.23. Found: C, 52.74; H, 5.80; N, 13.96.

The overall yield was 44.4 g. or 63%.

I claim:

1. A process for preparing 1,5(6)-substituted-2-aminobenzimidazoles of the formula I

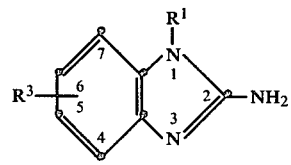

which comprises reacting a tautomeric benzimidazole of the formula II

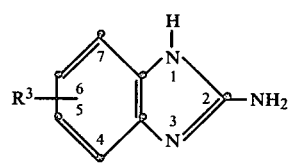

with a second reactant of the formula $X(CH_2)_nNCS$ in the presence of an alkali metal hydroxide or carbonate, water, and a water-miscible nonhydroxylic solvent at a temperature from about 0° C. to about 75° C., wherein $R^1$ is

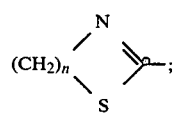

$R^2$ is $C_1$–$C_5$ alkyl, $C_3$–$C_7$ cycloalkyl, phenyl, furyl, or thienyl;

$R^3$ is at the 5- or 6-position and is hydrazinocarbonyl, carboxy, carboxamido, N-($C_1$–$C_4$ alkyl)carboxamido, hydroxymethyl, cyano, nitro, $C_1$–$C_4$ alkyl, $C_1$–$C_4$ alkoxy, $C_1$–$C_4$ alkylthio, methylsulfonyl, phenylthio, phenylsulfinyl, phenoxy, trifluoromethyl, $C_1$–$C_8$ alkoxycarbonyl, allyloxycarbonyl, propargyloxycarbonyl, ($C_3$–$C_7$ cycloalkyl)oxycarbonyl, ($C_3$–$C_7$ cycloalkyl)methoxycarbonyl, 1-($C_3$–$C_7$ cycloalkyl)ethoxycarbonyl, benzyloxycarbonyl, α-methylbenzyloxycarbonyl, phenoxycarbonyl, $C_1$–$C_8$ alkoxycarbonylmethyl, 1-($C_1$–$C_8$ alkoxycarbonyl)ethyl,

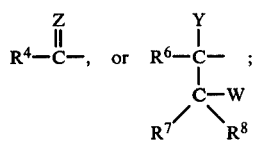

$R^4$ is hydrogen, $C_1$–$C_7$ alkyl, $C_3$–$C_7$ cycloalkyl, ($C_3$–$C_7$ cycloalkyl)methyl, 1-($C_3$–$C_7$ cycloalkyl)ethyl, thienyl, benzyl, phenyl, or mono-substituted phenyl wherein said substituent is selected from the group consisting of $C_1$–$C_4$ alkyl, $C_1$–$C_4$ alkoxy, chloro, bromo, iodo, nitro, and trifluoromethyl;

$R^6$ is hydrogen, $C_1$–$C_7$ alkyl, $C_3$–$C_7$ cycloalkyl, ($C_3$–$C_7$ cycloalkyl)methyl, 1-($C_3$–$C_7$ cycloalkyl)ethyl, phenyl, or mono-substituted phenyl, wherein said phenyl substituent is selected from the group consisting of $C_1$–$C_4$ alkyl, $C_1$–$C_4$ alkoxy, chloro, bromo, iodo, nitro, and trifluoromethyl;

$R^7$ and $R^8$ independently are hydrogen, halo, cyano, hydroxymethyl, nitro,

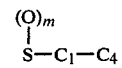

alkyl, $CH_2R^9$, $COR^9$, phenyl or mono-substituted phenyl, wherein said phenyl substituent is selected from the group consisting of $C_1$–$C_4$ alkyl, $C_1$–$C_4$ alkoxy, chloro, bromo, iodo, nitro, and trifluoromethyl;

$R^9$ is hydroxy, $C_1$–$C_4$ alkoxy, $C_3$–$C_6$ cycloalkyl-$C_1$–$C_4$ alkoxy, or $(O\text{-}C_1\text{-}C_4 \text{ alkyl})_p NR^{10}R^{11}$;

$R^{10}$ and $R^{11}$ independently are hydrogen or $C_1$–$C_4$ alkyl;

Z is oxygen, $C_1$–$C_4$ alkoxyimino, or $C_1$–$C_7$ alkylidene;

X is chloro or bromo;

Y is hydrogen and W is hydroxy, or together Y and W form a bond;

m is 0, 1, or 2;

n is 2 or 3; and p is 0 or 1.

2. The process of claim 1 wherein the second reactant is 3-bromopropyl isothiocyanate.

3. The process of claim 1 wherein the water-miscible nonhydroxylic solvent is acetone.

4. The process of claim 1 wherein $R^3$ is benzoyl.

5. The process of claim 1 wherein the second reactant is 2-chloroethyl isothiocyanate.

6. The process of claim 1 wherein the alkali metal hydroxide is sodium hydroxide.

7. The process of claim 1 wherein the temperature is from about 20° C. to about 30° C.

8. The process of claim 2 wherein $R^3$ is benzoyl.

* * * * *